(12) United States Patent
Temple

(10) Patent No.: US 10,556,813 B2
(45) Date of Patent: Feb. 11, 2020

(54) METHOD FOR TREATING CONDENSED VAPOR STREAMS CONTAINING ODOROUS COMPOUNDS

(71) Applicant: Stephen R. Temple, Santa Cruz, CA (US)

(72) Inventor: Stephen R. Temple, Santa Cruz, CA (US)

( * ) Notice: Subject to any disclaimer, the term of this patent is extended or adjusted under 35 U.S.C. 154(b) by 0 days.

(21) Appl. No.: 16/030,768

(22) Filed: Jul. 9, 2018

(65) Prior Publication Data

US 2018/0312416 A1 Nov. 1, 2018

Related U.S. Application Data

(63) Continuation of application No. 14/274,682, filed on May 10, 2014, now Pat. No. 10,017,404, which is a continuation of application No. 12/684,870, filed on Jan. 8, 2010, now Pat. No. 8,753,566.

(60) Provisional application No. 61/143,724, filed on Jan. 9, 2009.

(51) Int. Cl.
| | |
|---|---|
| *A61L 9/03* | (2006.01) |
| *A61L 9/14* | (2006.01) |
| *C02F 1/04* | (2006.01) |
| *C02F 1/68* | (2006.01) |
| *C02F 1/72* | (2006.01) |
| *C11B 3/12* | (2006.01) |
| *F28C 1/00* | (2006.01) |
| *A61L 9/00* | (2006.01) |
| *C02F 101/32* | (2006.01) |
| *C02F 103/18* | (2006.01) |
| *C02F 103/32* | (2006.01) |
| *C02F 103/22* | (2006.01) |

(52) U.S. Cl.
CPC .............. *C02F 1/72* (2013.01); *A61L 9/00* (2013.01); *C02F 1/725* (2013.01); *A61L 9/03* (2013.01); *A61L 9/145* (2013.01); *A61L 2209/211* (2013.01); *C02F 1/041* (2013.01); *C02F 1/683* (2013.01); *C02F 2101/322* (2013.01); *C02F 2103/18* (2013.01); *C02F 2103/22* (2013.01); *C02F 2103/32* (2013.01); *C02F 2303/02* (2013.01); *C11B 3/12* (2013.01); *F28C 1/00* (2013.01)

(58) Field of Classification Search
CPC ... A61L 9/00; A61L 9/03; A61L 9/145; A61L 2209/211; C02F 1/041; C02F 1/683; C02F 1/72; C02F 1/725; C02F 2101/322; C02F 2103/18; C02F 2103/22; C02F 2103/32; C02F 2303/02; C11B 3/12; F28C 1/00
See application file for complete search history.

(56) References Cited

U.S. PATENT DOCUMENTS

2004/0232007 A1* 11/2004 Carson ................ C02F 1/4672
205/688

* cited by examiner

*Primary Examiner* — Lucas A Stelling
(74) *Attorney, Agent, or Firm* — Owens Law Firm, PC

(57) ABSTRACT

The invention relates to methods and apparatuses for treating a condensate stream from a condenser that contains odorous compounds, such as various condensate streams produced in a rendering process. In one embodiment, the condensate stream is treated by adding an oxidizer to the liquid condensate stream to oxidize odor-causing compounds in the stream prior to being treated in a waste water pre-treatment system. In this manner, the odor resulting from these compounds can be reduced or eliminated.

12 Claims, 3 Drawing Sheets

METHOD FOR TREATING CONDENSED VAPOR STREAMS CONTAINING ODOROUS COMPOUNDS

This application is a continuation of U.S. application Ser. No. 14/274,682 filed May 10, 2014, which is a continuation of U.S. application Ser. No. 12/684,870 filed Jan. 8, 2010, now U.S. Pat. No. 8,753,566, which claims the benefit of U.S. Provisional Application No. 61/143,724, filed Jan. 9, 2009, the entireties of each of which are hereby incorporated by reference herein.

BACKGROUND OF THE INVENTION

Field of the Invention

The invention relates to methods for treating condensed vapor streams containing odorous vapors. In particular, the invention relates to methods for oxidizing condensate streams in, for example, rendering or pet food manufacturing facilities.

Description of Related Art

Control of odors is one of the most challenging problems faced by the animal byproduct processing industry, referred to as rendering. In most facilities animal byproduct is brought into the processing facility and processed to, in some cases, manufacture animal feed. The process converts the byproduct, which consists of waste animal tissue, into stable value-added material like purified animal fats (lard, tallow, and grease) and protein meals (meat, bone meal, and blood meal). Generally, the process is performed by simultaneously drying the animal byproduct and separating the fat from the bone and protein. In some cases, the animal tissue may be blended with other organic material to form feeds. In some cases the animal byproduct includes feathers and hair, and the processing of these materials includes hydrolyzing and drying the material to form feather meal and a hair meal.

In the process of drying the animal byproduct, heat is added to the material resulting in the generation of vapors. These vapors carry odorous compounds such as hydrogen sulfide, ammonia, and volatile organic compounds (VOCs). In most facilities an air scrubbing process is used to reduce or remove some of these odorous vapors prior to their release into the atmosphere. In addition, various vapor streams containing these odorous compounds are condensed to separate as many of the condensable vapors from the non-condensable vapors prior to air scrubbing or release to the atmosphere. This greatly reduces the load to the air scrubbing equipment and the environment. It should be appreciated that a rendering facility may generate multiple condensate streams from various process steps. For example, condensate streams may be produced from condensers used in conjunction with a cooker, an evaporator, a disk dryer, a spray dryer, drum dryer, or any other process step in which a vapor stream is produced and can be condensed.

In the process of condensing a vaporous stream, a large portion of the odorous or odor causing compounds are separated prior to air scrubbing thereby forming one or more liquid condensate streams containing these soluble, odor causing compounds. The condensed vapor streams typically are mixed with other waste streams and processed using a waste water pretreatment system, introduced into a biological system for processing, or discharged to a sewer system. In none of these cases, however, are the condensed vapor or condensate streams treated for odor prior to being fed to the waste water pre-treatment system. Therefore, even after mixing with other streams and being further processed prior to discharge, the soluble odor-causing compounds in these condensate streams can be the cause of odor problems in the surrounding atmosphere. In many cases where the condensed vapors from the processing of the animal byproduct material are mixed with other fluid systems and processed in a waste water pretreatment or in a biological treatment system, the odor-causing compounds are liberated through reduced solubility driven by changes in pH, temperature, mechanical aeration, or other means. Accordingly, once liberated, these compounds become an evident source of odor nuisance.

Therefore, there is a need for a method of treating the odor-causing compounds in condensate streams, as such need exists in rendering and pet food processing facilities, as well as other industries that produce vapor streams containing odor compounds that can be condensed, such as oil recovery processes.

BRIEF SUMMARY OF THE INVENTION

Generally, the invention and its various embodiments relate to methods and apparatuses for treating vapor streams comprising odorous compounds. More specifically, these vapor streams are condensed along with at least some of the odorous compounds to generate a liquid stream that is subsequently oxidized to reduce its odor.

In some embodiments, the invention relates to methods and apparatuses for treating a condensate stream from a condenser in a rendering process. Because the condensate streams generated in a rendering process contain a significant amount of odor-causing compounds, these condensate streams can be the cause of odor problems in the surrounding atmosphere, even after mixing with other liquid streams from the rendering process and after treatment of all of these combined streams prior to discharge. Accordingly, in one embodiment, a method for reducing odor-causing compounds in a condensate stream from a rendering process comprises condensing a vapor stream containing odorous compounds in a rendering process to produce a liquid condensate stream comprising soluble odor-causing compounds condensed from said vapor stream and adding an oxidizer to the condensate stream. As a result of adding an oxidizer, the odor-causing compounds are oxidized, thereby reducing the odor of the condensate stream. The oxidized condensate stream may then be fed to a waste water pre-treatment system or similar system or, in some cases, simply discharged.

In another embodiment, the oxidized condensate stream may optionally be mixed with other liquid streams from the rendering process and then fed to a waste water pre-treatment system or similar system, or in some cases, simply discharged. These other liquid streams may include any liquid stream from the rendering process, including streams that are intended to be discharged as well as other condensate streams from the rendering process that may also have been separately oxidized to remove odor-causing compounds. In other embodiments, these other condensate streams may be added to the oxidized condensate stream without having been oxidized or treated. In other embodiments, the oxidized condensate stream or streams can be added to the liquid effluent stream from a waste water pre-treatment system or similar system. It should be appreciated, again, that these various methods and apparatuses can be applied to any condensate stream in the rendering process and that such streams can be combined and treated collectively or treated separately and combined before feeding to a waste water pre-treatment system or its liquid effluent or before being discharged.

In other embodiments, a chelating agent may be added to the condensate stream to enhance the effectiveness of the oxidizer. For example, a chelating agent may be added to the condensate stream to increase the solubility of the oxidizer. Further, a chelating agent may be added to the condensate stream to enhance the solubility of a catalyst that is added to catalyze the oxidation of the condensate stream. Further still, a chelating agent may be added to prevent or reduce the formation of undesirable complexes that may interfere with the oxidation. For example, in connection with the use of hydrogen peroxide as an oxidizer and the use of a metal-based catalyst to catalyses the decomposition of the hydrogen peroxide to form hydroxyl radicals, a semi-colloidal metal complex may form during the oxidation process that, in some instances, may be undesirable. A chelating agent may be added to prevent the formation of such metal hydroxides or other insoluble metal complexes.

By oxidizing a condensate stream containing odorous components, odor treatment costs can be reduced and odor-causing compounds can be oxidized to reduce or eliminate odor problems caused by these compounds. In addition, particular odor-causing compounds can be targeted for treatment. Accordingly, any odor problems resulting from these compounds can be reduced or eliminated.

DETAILED DESCRIPTION OF THE INVENTION

Figure 1:
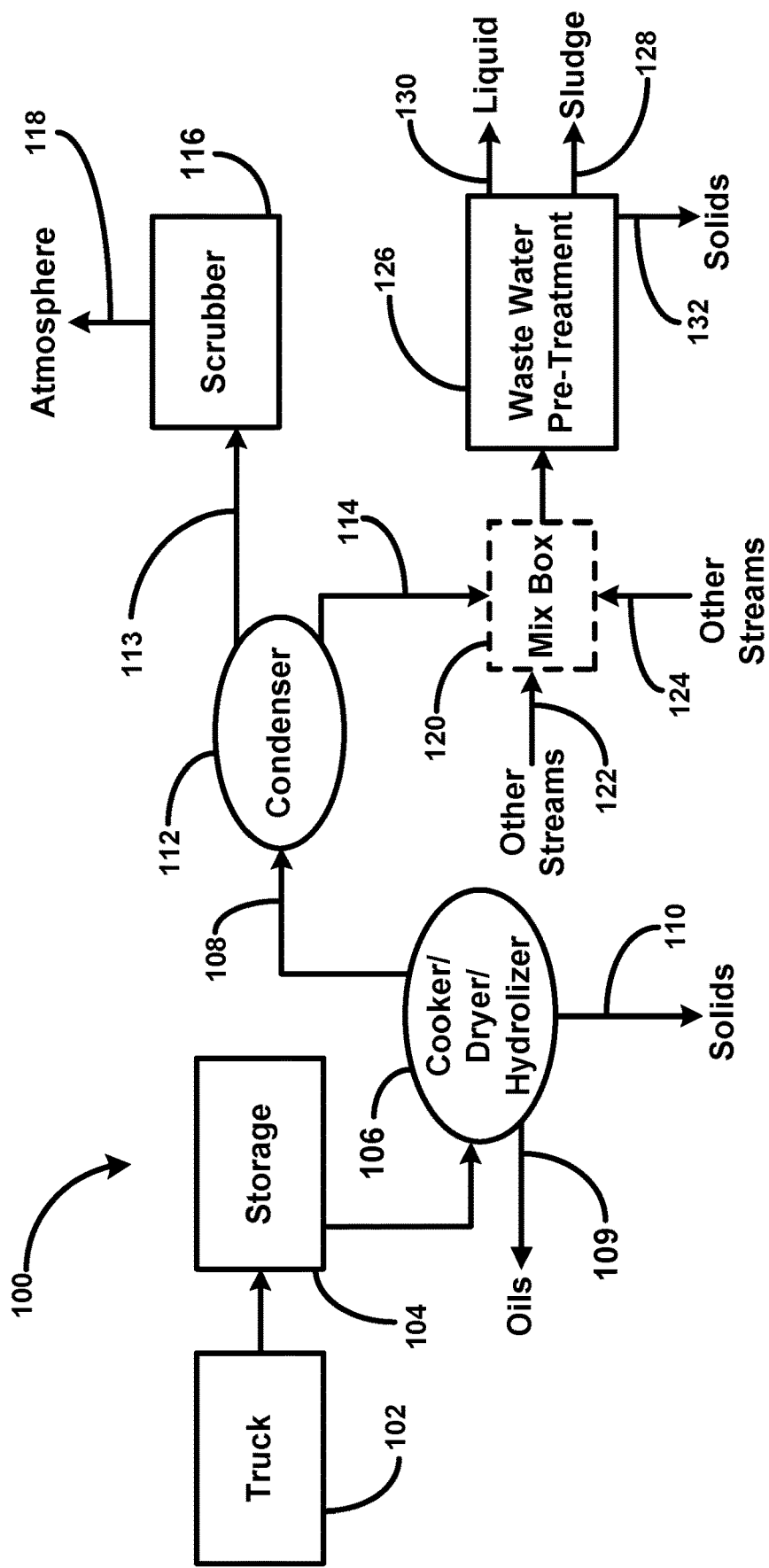
FIG. 1 is a flow diagram for a typical rendering process.

Some of the various embodiments of the invention are described below in conjunction with the Figures; however, this description should not be viewed as limiting the scope of the present invention. Rather, it should be considered exemplary of various embodiments that fall within the scope of the present invention as defined by the claims. Further, it should be appreciated that references to "the invention" or "the present invention" should not be construed as meaning that the description herein is directed to only one embodiment or that every embodiment must contain a given feature described in connection with the use of such phrases. In fact, various embodiments with common and differing features may be described herein.

Generally, the invention and its various embodiments relate to methods and apparatuses for treating vapor streams comprising odorous compounds. More specifically, these vapor streams are condensed along with at least some of the odorous compounds to generate a liquid stream that is subsequently oxidized to reduce its odor.

In some embodiments, the invention relates to methods and apparatuses for treating a condensate stream from a condenser in a rendering process. Because the condensate stream generated in a rendering process contains a significant amount of odor-causing compounds, this condensate stream can be the cause of odor problems in the surrounding atmosphere, even after mixing with other liquid streams from the rendering process and after treatment of all of these combined streams prior to discharge. Accordingly, in one embodiment, the condensate stream is treated to reduce odor and then optionally mixed with other liquid streams from the rendering process, which may be sent to a waste water pre-treatment system or, in some cases, discharged. Generally, the treatment of the condensate stream to reduce its odor comprises oxidizing the condensate stream by adding an oxidizer, with the optional addition of a catalyst to catalyze the oxidation and the optional addition of a chelating agent for various purposes as described further below. As a result of adding an oxidizer, the odor-causing compounds are oxidized, thereby reducing the odor of the condensate stream. The oxidized condensate stream may then be fed to a waste water pre-treatment system or similar system or, in some cases, simply discharged.

In other embodiments, the oxidized condensate stream may optionally be mixed with other liquid streams from the rendering process and then fed to a waste water pre-treatment system or similar system, or in some cases, simply discharged. These other liquid streams may include any liquid stream from the rendering process that is intended to be discharged, as well as other condensate streams from the rendering process that may also have been separately oxidized to remove odor-causing compounds. In other embodiments, these other condensate streams may be added to the oxidized condensate stream without having been oxidized or treated. In other embodiments, the oxidized condensate stream or streams can be added to the liquid effluent stream from a waste water pre-treatment system or similar system. It should be appreciated, again, that these various methods and apparatuses can be applied to any condensate stream in the rendering process and that such streams can be combined and treated collectively or treated separately and combined before feeding to a waste water pre-treatment system or its liquid effluent or before being discharged. Each of these embodiments is described in additional detail below in connection with the Figures.

FIG. 1 is a flow diagram for a typical rendering process. In this process 100, a truck 102 will typically dump various animal byproduct material into a storage tank 104. This byproduct material is feed to a cooker 106, or a rotary or disk dryer or hydrolizer, where heat is added to dry the material or to drive off the water content and to separate the fat from the bone and protein. As a result, the cooker 106 produces a vapor stream 108, an oils stream, and a solids stream 110 that is further processed into various products, such as animal feed. It should be appreciated that if a rotary or disk dryer or hydrolizer is used then typically only two streams are produced, a vapor stream and a solids stream that also comprises oils.

The vapor stream 108 is passed to a condenser 112 where the vapor stream 108 is cooled to condense the vapor stream, thereby separating as many of the condensable vapors from the non-condensable vapors. The condenser 112 produces a vapor stream 113 that is passed to an air scrubber 116 where certain vaporous components are removed from the vapor. The air scrubber 116 then discharges the remaining vapor 118 to the atmosphere. It should be appreciated that instead of a scrubber 116, or in combination with a scrubber, the vapor stream 113 may be treated by partially burning the vapor stream 113 in either a boiler as part of the air fed to the boiler for combustion, a thermal oxidizer (TO), or a regenerative thermal oxidizer (RTO) and then emitted to the atmosphere as an incompletely combusted exhaust stream or further treated using a scrubber.

The condenser 112 also produces a condensate stream 114 that is passed to a mix box 120 into which other process streams 122, 124 from the rendering process 100 are added. The combination of all of these streams in the mix box 120 is then passed to a waste water pre-treatment system 126 that separates sludge 128, liquid 130, and solids 132 from each other for discharge. It should be appreciated that the waste water pre-treatment system 126 may be a diffused or induced air flotation system because the solids and oil are more likely to separate and float than separate and sink. In some cases pre-treatment may include biological digestion of the soluble fraction that is measured as biological oxygen demand, as well as the use of nitrifying bacteria to remove the nitrogen loading prior to surface discharge of discharge to a municipality.

It should be appreciated that the use of a mix box 120, shown in FIG. 1 with a dashed line, is optional since the condensate stream 114 may be passed directly to the waste water pre-treatment system 126. Further any additional process streams 122, 124 may also be passed directly to the waste water pre-treatment system 126. Alternatively, any of the condensate stream 114 or other process streams 122, 124 may simply be added to each other and passed to the waste water pre-treatment system 126 without the use of a mix box 120.

It should be appreciated that the additional process streams 122, 124 may be any process stream produced in the rendering process, including, for example, any liquid stream generated in the rendering process that is intended to be discharged such as wash water as well as other condensate streams from the rendering process that may also have been separately oxidized to remove odor-causing compounds. For example, any vaporous stream produced through the processing of any animal parts to which heat is added resulting in the generation of a vaporous stream that would contain odorous components, at least a portion of which could be subsequently condensed.

Figure 2:
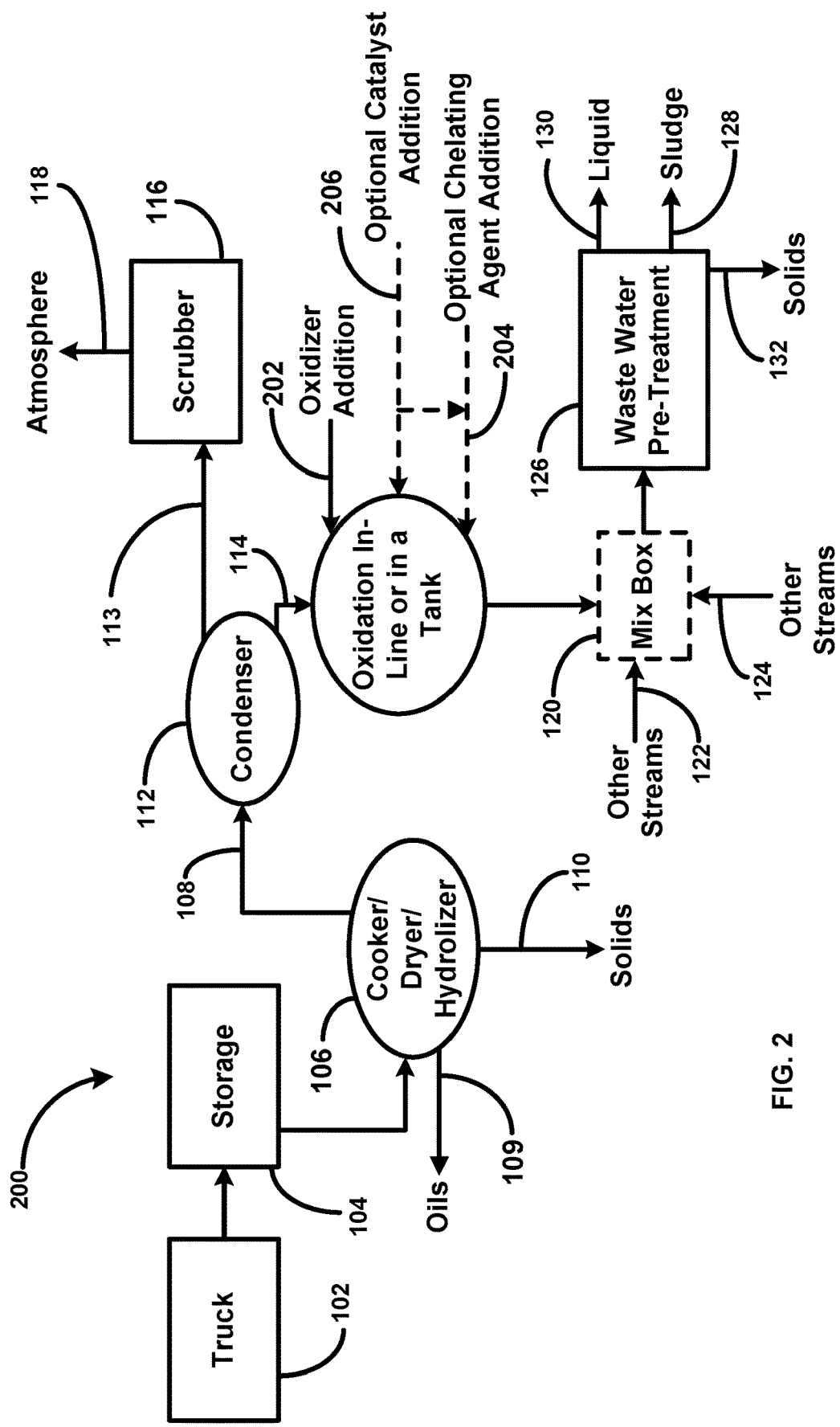
FIG. 2 is a flow diagram of one embodiment of the present invention.

FIG. 2 is a flow diagram of one embodiment of the present invention. In this rendering process 200 basically all of the same steps as described above in connection with FIG. 1 are used. However, the condensate stream 114 is oxidized prior to being added to the mix box 120. By oxidizing this condensate stream 114 odor-causing compounds can be oxidized to reduce or eliminate odor problems caused by these compounds thereby reducing odor treatment costs. Additional information regarding odors and volatile organic compounds from a rendering plant are described in "Effect of a Packed-Bed Scrubber Using Radox Catalyst on the Emission of Odors and Volatile Organic Compounds from a Commercial Poultry Rendering Plant," by James A. Zahn and Jennifer Anhalt, April 2002, National Swine Research and Information Center, USDA-ARS, 2150 Pammel Drive, Ames, Iowa 50011, United States Department of Agriculture, the entirety of which is hereby incorporated by reference. It should be appreciated that the odorous compounds discussed in this paper are some of the compounds that can be oxidized according to the various embodiments of the present invention.

The oxidation of the condensate stream 114 can be accomplished by adding an oxidizer 202 directly to the condensate stream 114 upstream of the mix box 120 thereby oxidizing the condensate stream 114 before it is added to the mix box 120. Many oxidizers are available for this oxidation step. For example, oxidizers that may be used include, but are not limited to, bromine, chlorine, hypochlorous acid, chlorine dioxide, permanganate, ozone, perhydroxial radical, and hydrogen peroxide alone or hydrogen peroxide and hydroxyl radicals generated by the addition of hydrogen peroxide and a catalyst that catalyzes the decomposition of hydrogen peroxide. Information regarding the addition of oxidizers and catalysts to oxidize odorous and noxious components absorbed from a gas stream is described in U.S. patent application Ser. No. 11/442,554, entitled Method and Apparatus for Use of Reacted Hydrogen Peroxide Compounds in Industrial Process Waters (U.S. Publication No. 2007/0059229), the entirely of which is hereby incorporated by reference herein. It should be appreciated that multiple oxidizers may be used, including any combination of the foregoing named oxidizers.

The oxidizer 202 can be added directly to the condensate stream 114. The addition point in the condensate stream 114 where the oxidizer 202 is added should be at a location upstream of the mix box 120 that provides sufficient time for the oxidizer to contact and oxidize a desired amount of the odor-causing compounds prior to the condensate stream 114 reaching the mix box 120. Accordingly, the addition point will be determined based upon the concentration of odor-causing compounds in the condensate stream 114, the amount of oxidation desired, the amount of oxidizer added, and the residence time available for oxidation to occur. One of skill in the art will appreciate how to optimize these parameters to achieve the optimal or desired reduction in odor.

It should also be appreciated that the oxidation of the condensate stream 114 may be performed in a separate tank by feeding the condensate stream 114 to an appropriately sized tank and adding the oxidizer to the tank. The oxidized condensate can then be fed from the tank to the mix box 120. In this case, the tank may provide better control over the mixing and contacting of the oxidizer with the odor-causing compounds. The tank should be appropriately sized to provide sufficient residence time to accomplish the desired degree of oxidization based upon the concentration of odor-causing compounds in the condensate stream 114, the amount of oxidation desired, and the amount of oxidizer added. It should be appreciated, however, that a portion of the oxidation may be performed in a tank and additional oxidation may occur in the condensate stream 114 discharged from the tank. In other words, the tank does not necessarily have to be sized to provide all of the desired oxidation and instead can be sized such that the oxidation occurring in the tank as well as in the condensate stream leaving the tank prior to its addition to the mix box provides the overall desired degree of oxidation.

In addition, a chelating agent may optionally be added to the condensate stream 114 for a variety of purposes. For example, in connection with the use of hydrogen peroxide as an oxidizer and the use of a metal-based catalyst to catalyze the decomposition of the hydrogen peroxide to form hydroxyl radicals, a semi-colloidal metal complex may form during the oxidation process, and in some instances, the development of this colloidal metal complex is undesirable. A chelating agent may be added to prevent the formation of metal hydroxides or other insoluble metal complexes. In one embodiment, the chelating agent may be organic acids such as gluconic acids, glycolic acids, lactic acids, and combinations thereof. It will be appreciated that the chelating agent may be selected from a large number of available chelating agents; however, the chelating agent should not be of such potent chelating ability as to prevent the availability of the metal complex for decomposition purposes.

Chelating agents can also be selected and used based upon the particular oxidizer being used. For example, a chelating agent may be added to enhance the solubility of the oxidizer or any catalyst that is used in conjunction with the oxidizer. For example, chelating agents known in the art may be used to increase the solubility of metal-based catalysts, such as ferrous ion and other metal complexes, particularly useful in conjunction with the use of hydrogen peroxide as the oxidizer. In addition, ferric ($Fe^{3+}$) ion may be used to decompose hydrogen peroxide to produce hydroxyl radicals, and chelating agents may be added to increase the solubility of the ferric ion, thereby increasing the production of hydroxyl free radicals. Chemical Treatment of Pesticide Wastes—Evaluation of Fe(III) Chelates for Catalytic Hydrogen Peroxide Oxidation of 2,4-D at Circumneutral pH, Sun et al., J. Agric. Food Chem., 1992, 40, 322-327, the entirety of which is hereby incorporated by reference herein, describes several chelating agents that may be used to solubilize ferric ion. Such chelating agents that showed "high" catalytic activity and that may be used include: aminopolycarboxylates, such as nitrilotriacetic acid and hydroxyethyliminodiacetic acid; N-heteroxcyclic carboxylates, such as picolinic acid; polyhydroxy aromatics, such as gallic acid; and other compounds, such as rhodizonic acid, tetrahydroxy-1,4-quinone, and hexaketocyclohexane. Another chelating agent that may be used is ferric methylglycinediacetate (Fe-MGDA), which is further described in U.S. Pat. No. 6,960,330, the entirety of which is hereby incorporated by reference herein. These chelating agents may be used separately; however, it may be possible to use mixtures of these chelating agents as well. The use of chelating agents in connection with the scrubbing of oxidize odorous and noxious components from gas streams is described in U.S. patent application Ser. No. 11/442,554, entitled Method and Apparatus for Use of Reacted Hydrogen Peroxide Compounds in Industrial Process Waters (U.S. Publication No. 2007/0059229), the entirety of which is hereby incorporated by reference herein.

There are several methods by which a chelating agent may be added. FIG. 2 illustrates the optional addition of a chelating agent 204 directly to the condensate stream 114. FIG. 2 also illustrates the optional addition of a catalyst 206 either directly to the condensate stream 114 or by adding it to the chelating agent 204. In either case, the chelating agent 204 and the catalyst 206 are added to the condensate stream 114 separately from the oxidizer 202. In the embodiment in which the chelating agent 204 and the catalyst 206 are added together prior to being added to the condensate stream 114, the combined chelating agent 204 and catalyst 206 should be added near the addition point of the oxidizer 202 and may be added immediately adjacent to the addition point of the oxidizer 202, either upstream or downstream of the addition point of the oxidizer 202. It should be appreciated that the mixing of the chelating agent and catalyst should be done in a manner to provide sufficient time for chelation to occur prior to adding this mixture to the condensate stream 114. Also, as shown in FIG. 2, each of the chelating agent 204, the catalyst 206, and the oxidizer 202 may be added separately to the condensate stream 114, noting that their relative addition points should be such that sufficient time is provided for chelation to occur to optimize catalyst activity. One of skill in the art will appreciate that the concentration and feed rates of the chelating agent and any catalyst can be optimized in conjunction with the concentration and feed rate of the oxidizer to provide the desired degree of oxidation, depending upon the addition point of the chelating agent and any catalyst and the oxidizer into the condensate stream 114.

If the condensate stream 114 is oxidized in a tank, the chelating agent 204 may be added to any catalyst 206, and the resulting mixture added to the tank separately from the addition of the oxidizer 202 to the tank. In this case, again, mixing of the chelating agent 204 and catalyst 206 should be done to provide sufficient time for chelation to occur prior to adding this mixture to the condensate stream 114 in the oxidation tank. In yet another embodiment, each of these components may be added separately to the tank. One of skill in the art will appreciate that the concentration and feed rates of the chelating agent and any catalyst into the tank can be optimized in conjunction with the concentration and feed rate of the oxidizer into the tank and the size and residence time of the tank to provide the desired degree of oxidation.

As described above, when using a catalyst with the oxidizer, the chelating agent and the catalyst, such as ferrous ion or ferric ion (which may be added, for example, as ferric sulfate) may be mixed before use to allow for chelation. In this case, the selection of the catalysis and the chelating agent can be based upon the specific application or particular components to be oxidized. By mixing the catalyst and the chelating agent prior to use, this mixture is essentially "tailor-made" and is ready for immediate use in the particular application at issue. In fact, this mixture can be prepared remote from the facility where it will be used and shipped to that facility for immediate use.

In some embodiments, control over the desired degree of oxidation can be accomplished using colorimetric measurement of one or more odor causing compounds. In this case, oxidation of a given odor causing compound to an end point could be used to adjust the concentration and feed rate of the oxidizer, the chelating agent, or both for a given addition point or tank size.

In some embodiments, an electrode could be used to monitor the concentration of a given odor causing compound, or its absorbed form, to similarly adjust the feed rate of the oxidizer, the chelating agent, or both for a given addition point or tank size. For example, a THERMO ORION silver/sulfide ion selective electrode could be used to monitor sulfide (i.e., a measure of solubilized hydrogen sulfide), and the feed rate of the oxidizer could be adjusted based on the presence of sulfide as measured by the probe.

In some embodiments, hydrogen peroxide can be used as the oxidizer. In this case, a hydrogen peroxide sensing system could be used to monitor the hydrogen peroxide addition rate. For example, a PROMINENT DULCOTROL PEROX 20 hydrogen peroxide sensing and control system or the like could be used to control the addition of hydrogen peroxide, particularly in those cases where conventional use of ORP (oxidation reduction potential) is ineffective at monitoring either hydrogen peroxide addition or the decomposition of the hydrogen peroxide with a catalyst. In one embodiment, hydrogen peroxide could be added at a rate to simply maintain a detectable amount of hydrogen peroxide using this control system. It should be appreciated, however, that ORP may be used to control the addition rate of the oxidizer. In this case, the ORP measurement can be used to determine whether additional oxidizer is required to provide the requisite oxidation residual potential.

Similar to the process shown in FIG. 1, the condensate stream 114, after having been oxidized, is passed to a mix box 120 into which other process streams 122, 124 from the rendering process 100 are added. As described above, these additional process streams 122, 124 may include any stream produced in the rendering process, including streams that are intended to be discharged, as well as other condensate streams from the rendering process that may also have been separately oxidized to remove odor-causing compounds. For example, such condensate streams may include any condensate stream produced from a vaporous stream generated in the rendering process, such as any vaporous stream generated by the heating of animal parts, other than the cooker 106, that may also contain odorous components. These other condensate streams may be added to the oxidized condensate stream 114 without having been oxidized or treated. Alternatively, one or more of these other condensate streams may be treated, separately or in combination, through oxidation in the same manner as the condensate stream 114 from the cooker 106. In fact, it should be appreciated that although this description is focused primarily on the condensate stream 114 from the cooker 106, the various embodiments described herein apply equally to any other condensate stream containing odorous compounds that is generated, or that could be generated, in the rendering process.

As described above in connection with FIG. 1, the use of the mix box 120 in the process shown in FIG. 2 is also optional. Accordingly, the condensate stream 114 may be passed directly to the waste water pre-treatment system 126. Further any additional process streams 122, 124 may also be passed directly to the waste water pre-treatment system 126. Alternatively, any of the condensate stream 114 or other process streams 122, 124 may simply be added to each other and passed to the waste water treatment system 126 without the use of a mix box 120.

Figure 3:
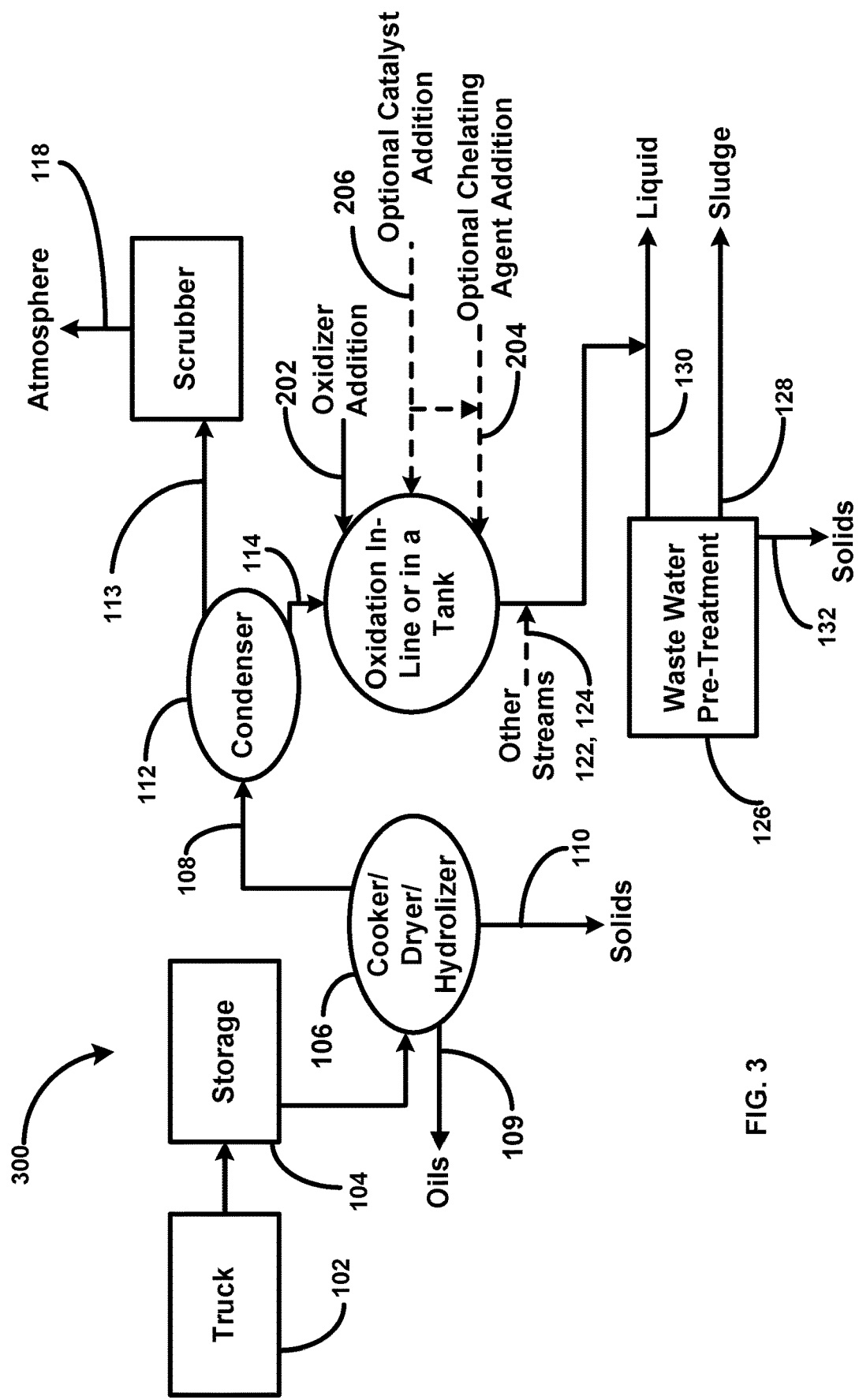
FIG. 3 is a flow diagram of another embodiment of the present invention.

FIG. 3 is a flow diagram of another embodiment of the present invention. The process 300 shown in FIG. 3 is similar to that shown in FIG. 2, with the exception that the oxidized condensate stream 114 is added directly to the effluent liquid stream 130 produced by the waste water pre-treatment system 126. This embodiment provides the ability to potentially lower the biological oxygen demand of the effluent liquid stream 130 due to the addition of the oxidized condensate stream 114. Further, since the effluent liquid stream 130 from the waste water pre-treatment system 126 typically requires the addition of acid to reduce its pH prior to discharge, the addition of the oxidized condensate stream 114 may reduce the amount of acid required to reduce the pH. This occurs because the condensate stream 114 typically has a relatively high concentration of ammonia and, therefore, a relatively high pH. Further still, by adding the oxidized condensate stream 114 downstream of the waste water pre-treatment system 126, the load on the waste water pre-treatment system 126 is reduced, thereby reducing the wear on the waste water pre-treatment system 126 and potentially reducing operating and maintenance costs.

In this embodiment, other streams 122, 124, as described above, but, in particular, other condensate streams from the rendering process that also have been separately oxidized to remove odor-causing compounds, can optionally be added to the liquid effluent stream 130 from the waste water pre-treatment system 126 or similar system. It should be appreciated, that these other streams 122, 124 can be added directly to the condensate stream 114 or separately to the liquid effluent stream 130. Further, as described above, one or more of these condensate streams can be combined and treated collectively by oxidation as described in connection with FIG. 2 and then added to the liquid effluent stream 130.

While the foregoing description has generally been in the context of a condensate stream in a rendering facility, it should be appreciated that the process and methods described herein may have application in treating other liquid streams containing dissolved odorous compounds. For example, such streams exist in the pet food manufacturing industry and animal kill plants, and these streams can be similarly treated using the various embodiments of the invention described herein. Therefore, the foregoing description should not be viewed as limited to the rendering industry or any particular liquid stream and may have application for any vapor stream generated by a process that has an odor load that is condensable and that can be oxidized, such as oil recovery processes.

What is claimed is:

1. A method for reducing odor-causing compounds in a rendering process, comprising:
    condensing a first vapor stream produced in a rendering process comprising at least one vaporous odor-causing compound to condense at least a portion of said first vapor stream and said at least one vaporous odor-causing compound to produce a first condensate stream comprising at least one soluble odor-causing compound condensed from said first vapor stream;
    adding an oxidizer to said first condensate stream to oxidize said at least one soluble odor-causing compound;
    condensing at least a portion of a second vapor stream produced in the rendering process to produce a second condensate stream;
    mixing said first condensate stream and said second condensate stream to produce a combined condensate stream; and
    discharging said combined condensate stream from the rendering process, wherein said discharging comprises adding said combined condensate stream to a liquid effluent from a waste-water pre-treatment system.

2. The method of claim 1, wherein said second vapor stream comprises at least one vaporous odor-causing compound and wherein said condensing said second vapor stream condenses said at least one vaporous odor-causing compound in said second vapor stream to produce said second condensate stream, wherein said second condensate stream comprises at least one soluble odor-causing compound condensed from said second vapor stream.

3. The method of claim 2, further comprising:
    adding a second oxidizer to said second condensate stream to oxidize said at least one soluble odor-causing compound condensed from said second vapor stream.

4. The method of claim 1, wherein an acid addition requirement of the waste-water pretreatment system is less than an acid addition requirement of the waste-water pre-treatment system operated without said adding said combined condensate stream to the liquid effluent from the waste-water pre-treatment system.

5. The method of claim 1, further comprising:
    measuring a sulfide concentration to produce a measured sulfide concentration; and
    controlling a rate of said adding of the oxidizer to said first condensate stream based upon said measured sulfide concentration.

6. The method of claim 1, wherein the oxidizer comprises hydrogen peroxide, and further comprising:
    measuring a peroxide concentration of said first condensate stream after said adding the oxidizer to produce a measured peroxide concentration; and
    controlling a rate of said adding of the oxidizer to said first condensate stream based upon said measured peroxide concentration.

7. A method for reducing odor-causing compounds in a rendering process, comprising:
    condensing a first vapor stream produced in a rendering process comprising at least one vaporous odor-causing compound to condense at least a portion of said first vapor stream and said at least one vaporous odor-causing compound to produce a first condensate stream comprising at least one soluble odor-causing compound condensed from said first vapor stream;

condensing at least a portion of a second vapor stream produced in the rendering process to produce a second condensate stream;

mixing said first condensate stream and said second condensate stream to produce a combined condensate stream;

adding an oxidizer to said combined condensate stream, thereby oxidizing said at least one soluble odor-causing compound condensed from said first vapor stream; and discharging said combined condensate stream from the rendering process, wherein said discharging comprises adding said combined condensate stream to a liquid effluent from a waste-water pre-treatment system.

8. The method of claim 7, wherein said second vapor stream comprises at least one vaporous odor-causing compound, wherein said condensing said at least a portion of said second vapor stream condenses said at least one vaporous odor-causing compound in said second vapor stream to produce said second condensate stream, wherein said second condensate stream comprises said at least one soluble odor-causing compound condensed from said second vapor stream, and wherein said adding the oxidizer to said combined condensate stream oxidizes said at least one soluble odor-causing compound condensed from said second vapor stream.

9. The method of claim 7, wherein an acid addition requirement for the waste-water pre-treatment system is less than an acid addition requirement of the waste-water pre-treatment system operated without said adding said combined condensate stream to the liquid effluent from the waste-water pre-treatment system.

10. The method of claim 7, further comprising:
measuring a sulfide concentration to produce a measured sulfide concentration; and
controlling a rate of said adding of the oxidizer to said combined condensate stream based upon said measured sulfide concentration.

11. The method of claim 7, wherein the oxidizer comprises hydrogen peroxide, and further comprising:
measuring a peroxide concentration of said combined condensate stream after said adding the oxidizer to produce a measured peroxide concentration; and
controlling a rate of said adding of the oxidizer to said combined condensate stream based upon said measured peroxide concentration.

12. A method for reducing odor-causing compounds in a rendering process, comprising:

condensing a vapor stream produced in a rendering process comprising at least one vaporous odor-causing compound to condense at least a portion of said vapor stream and said at least one vaporous odor-causing compound to produce a condensate stream comprising at least one soluble odor-causing compound condensed from said vapor stream;

mixing said condensate stream with a liquid stream generated in the rendering process to produce a combined liquid stream;

adding an oxidizer to said combined liquid stream to oxidize said at least one soluble odor-causing compound; and discharging said combined liquid stream from the rendering process, wherein said discharging comprises adding said combined liquid stream to a liquid effluent from a waste-water pre-treatment system.

* * * * *